United States Patent [19]
Eckenhoff et al.

[11] Patent Number: 5,972,370
[45] Date of Patent: Oct. 26, 1999

[54] PEPTIDE/PROTEIN SUSPENDING FORMULATIONS

[75] Inventors: James B. Eckenhoff, deceased, late of Los Altos, by Bonnie J. Eckenhoff, executrix; Leslie A. Holladay, Mountain View; John Joseph Leonard, Jr., Cupertino; Iris K. M. Leung; Sally A. Tao, both of San Jose; Judy A. Magruder, Mountain View; John P. Carr, Sunnyvale; Jeremy C. Wright, Los Altos, all of Calif.

[73] Assignee: Alza Corporation, Palo Alto, Calif.

[21] Appl. No.: 09/238,159

[22] Filed: Jan. 28, 1999

Related U.S. Application Data

[62] Division of application No. 08/475,238, Jun. 7, 1995.

[51] Int. Cl.$^6$ .................. A61F 2/00; A61K 9/14; A61K 38/00; C07K 17/02
[52] U.S. Cl. ............. 424/424; 424/489; 424/499; 424/502; 514/2; 530/351
[58] Field of Search ............... 424/424, 489, 424/499, 502; 514/2; 530/351

[56] References Cited

U.S. PATENT DOCUMENTS

| | | | |
|---|---|---|---|
| 3,732,865 | 5/1973 | Higuchi et al. | 604/892.1 |
| 3,833,725 | 9/1974 | Thompson et al. | 424/243 |
| 4,036,954 | 7/1977 | Murakami et al. | 514/573 |
| 4,180,560 | 12/1979 | Katz et al. | 424/426 |
| 4,215,691 | 8/1980 | Wong | 424/432 |
| 4,237,885 | 12/1980 | Wong et al. | 424/432 |
| 4,389,414 | 6/1983 | Kent | 514/530 |
| 4,475,916 | 10/1984 | Himmelstein | 424/424 |
| 4,483,849 | 11/1984 | Carter et al. | 424/85.5 |
| 4,507,281 | 3/1985 | Asculai et al. | 424/85.7 |
| 4,526,938 | 7/1985 | Churchill et al. | 525/415 |
| 4,675,381 | 6/1987 | Bichon | 530/345 |
| 4,834,985 | 5/1989 | Elger et al. | 424/488 |
| 4,847,079 | 7/1989 | Kwan | 424/85.7 |
| 4,855,141 | 8/1989 | Eckenhoff et al. | 424/423 |
| 4,871,538 | 10/1989 | Yim et al. | 424/85.7 |
| 4,942,035 | 7/1990 | Churchill et al. | 514/15 |
| 4,954,342 | 9/1990 | Lattanzi et al. | 424/436 |
| 5,032,572 | 7/1991 | Saffran et al. | 514/3 |
| 5,034,229 | 7/1991 | Magruder et al. | 424/422 |
| 5,047,396 | 9/1991 | Orban et al. | 514/11 |
| 5,057,318 | 10/1991 | Magruder et al. | 424/438 |
| 5,081,156 | 1/1992 | Yamshira et al. | 514/773 |
| 5,096,926 | 3/1992 | Fiorini et al. | 514/569 |
| 5,110,596 | 5/1992 | Magruder et al. | 424/438 |
| 5,122,376 | 6/1992 | Aliverti et al. | 424/405 |
| 5,137,727 | 8/1992 | Eckenhoff | 424/422 |
| 5,211,950 | 5/1993 | Kobayashi et al. | 424/422 |
| 5,221,278 | 6/1993 | Linkwitz et al. | 604/890 |
| 5,223,265 | 6/1993 | Wong | 424/473 |
| 5,236,707 | 8/1993 | Stewart | 424/85.7 |
| 5,324,518 | 6/1994 | Orth et al. | 424/423 |
| 5,342,625 | 8/1994 | Hauer et al. | 424/455 |
| 5,360,616 | 11/1994 | Garza-Flores et al. | 424/489 |
| 5,614,487 | 3/1997 | Battersby et al. | 514/2 |
| 5,735,897 | 4/1998 | Buirge | 623/12 |

FOREIGN PATENT DOCUMENTS

| | | |
|---|---|---|
| 0 374 2 120 A3 | 6/1990 | European Pat. Off. . |
| 0281299 | 9/1988 | Japan . |
| 8809673 | 12/1988 | Japan . |
| 5238949 | 5/1993 | Japan . |
| 9908832 | 5/1993 | Japan . |
| 95/34285 | 12/1995 | WIPO . |

OTHER PUBLICATIONS

"The Pharmacological Basis of Therapeutics", by Goodman and Gilman, 7th Ed., pp. 1430–1439 (1985).
Seeburg, et al., "Efficient Bacterial Expression of Bovine and Procine Growth Hormones", *DNA*, 2:1, 37–45 (1983).
Woychik, et al., "Cloning and nucleotide sequencing of the bovine growth hormone gene", *Nucleic Acids Res.*, 10:2, 7197–7210 (1982).

*Primary Examiner*—Nancy Degen
*Assistant Examiner*—William Sandals
*Attorney, Agent, or Firm*—Mary Ann Dillahunty; Steven F. Stone; Pauline A. Clarke

[57] ABSTRACT

The present invention provides improved compositions for improving the chemical and physical stability of peptides and proteins. The invention provides a liquid beneficial agent formulation containing a liquid suspension comprising at least 5% by weight beneficial agent and having a viscosity and beneficial agent size which minimizes settling of the agent in suspension over the extended delivery period.

21 Claims, 2 Drawing Sheets

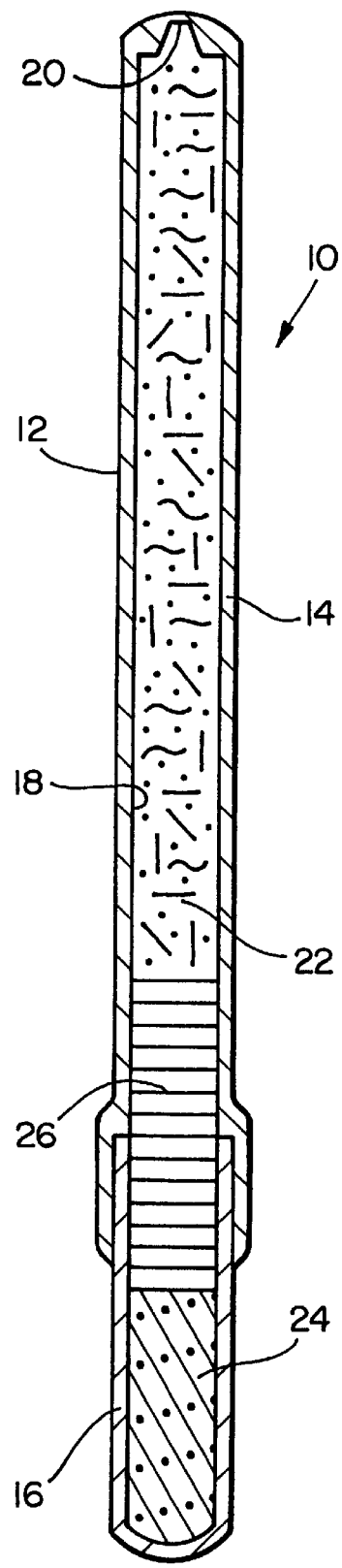
FIG_1

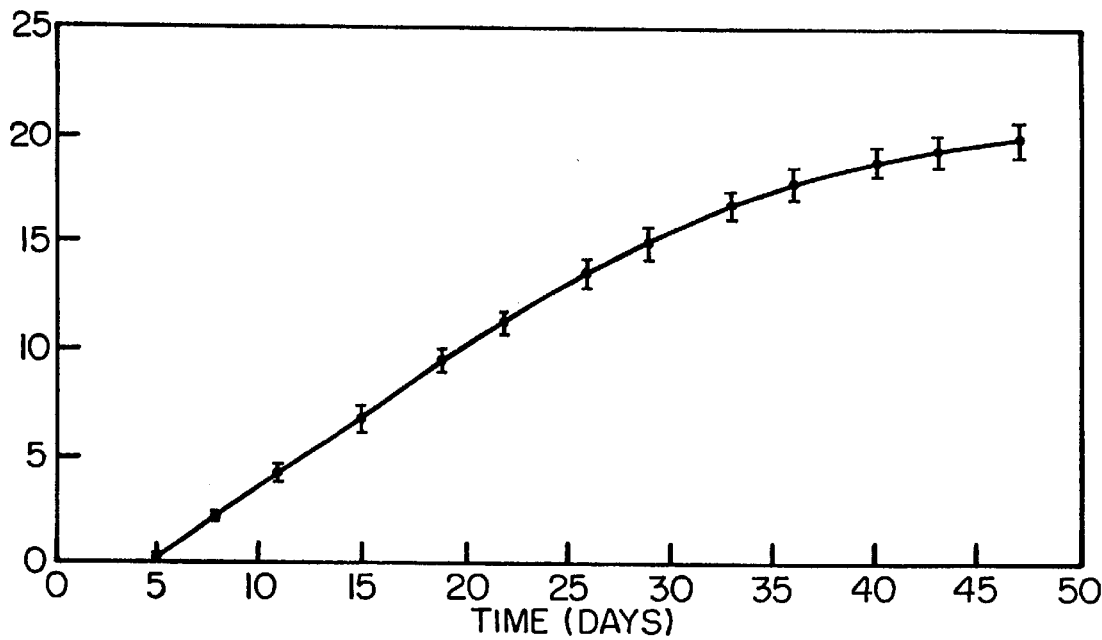
FIG_2
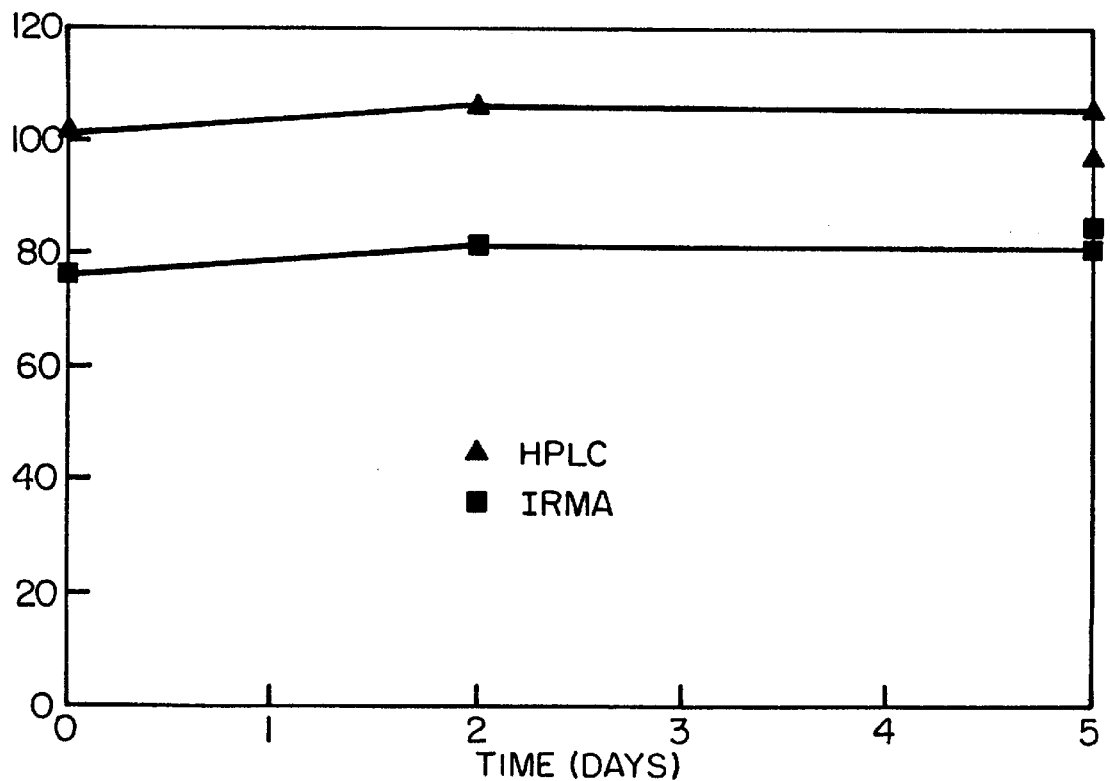
FIG_3

PEPTIDE/PROTEIN SUSPENDING FORMULATIONS

This application is a divisional of application Ser. No. 08/475,238, filed Jun. 7, 1995.

TECHNICAL FIELD

This invention relates to stabilized, concentrated suspensions formulations of peptides and proteins. More particularly, this invention relates to novel and improved compositions for providing concentrated, non-aqueous suspensions of peptides/proteins for pharmaceutical use having adequate chemical, physical and bioactive stability suitable for long term delivery from a sustained release drug delivery system.

BACKGROUND ART

Proteins, as well as many other biologically active compounds, degrade over time in aqueous solution. Because of this chemical instability, protein solutions are often not suitable for use in drug delivery devices. Carriers, in which proteins do not dissolve but rather are suspended, can often offer improved chemical stability. Furthermore, it can be beneficial to suspend the beneficial agent in a carrier when the agent exhibits low solubility in the desired vehicle. However, suspensions can have poor physical stability due to settling and agglomeration of the suspended beneficial agent. The problems with non-aqueous carriers tend to be exacerbated as the concentration of the active compound is increased.

For drug delivering implants, dosing durations of up to one year are not unusual. Beneficial agents which have low therapeutic delivery rates are prime candidates for use in implants. When the device is implanted or stored, settling of the beneficial agent in the liquid formulation can occur. This heterogeneity can adversely effect the concentration of the beneficial agent dispensed. Compounding this problem is the size of the implanted beneficial agent reservoir. Implant reservoirs are generally on the order of 25–250 $\mu$l. With this volume restriction, a formulation of high concentration (greater than or equal to 10%) and a minimum amount of suspension vehicle and other excipients is preferred.

Alpha interferon ($\alpha$-IFN) is one example of a beneficial agent which provides a therapeutic effect at a low dose. This interferon is indicated in the treatment of chronic hepatitis because of its antiviral activity. Prescribed therapy presently entails injections of $\alpha$-IFN solution, containing about 3.0$\times$10$^6$ IU (15 micrograms) of agent per dose, three times per week for a 4 to 6 month period. Frequent injections are required because of the short elimination half-life of $\alpha$-IFN; most of the drug being completely cleared from the plasma within eight to ten hours after the injection.

U.S. Pat. Nos. 4,871,538 issued to Yim et al; 4,847,079 issued to Kwan et al; 5,081,156 issued to Yamashira et al, and European Publication No. 0,281,299 issued to Yim et al describe IFN/peptide compositions with concentrations between $10^4$ to $10^8$ IU/ml. In Kwan et al a pharmaceutical solution having a $\alpha$-IFN concentration of $10^3$ to $10^8$ IU/ml is described. Yim describes a dosage range being between $10^4$ to $10^8$ IU $\alpha$-IFN/ml. In Yim II, an insoluble complex including $\alpha$-IFN, zinc, and protamine is suspended in a phosphate buffer. Yim I, Yim II, and Kuan, however, teach the use, in part, of an aqueous buffer in their compositions. This leads to possible hydrolysis of the compound, leading to chemical degradation and instability. Yamashira teaches a sustained release preparation of interferon in a n mixture with a biodegradable carrier. IFN is incorporated at concentrations of $10^3$ to $10^8$ IU per 1 mg of carrier or, alternatively, each dosage form containing $10^4$ to $10^9$ IU of interferon. Furthermore, while the patents and publications described above describe concentrations between $10^4$ to $10^9$ IU/ml, none describe concentrations on the order of $10^9$ to $10^{11}$ IU/ml.

There is a need for a novel composition comprising a nonaqueous suspension vehicle and concentrated protein/peptide as the beneficial agent for use in implanted, sustained release devices. While it is known in the art to achieve stable $\alpha$ IFN concentrations of up to $10^8$ IU/ml, this invention utilizes a novel combination whose combined effect produces a significant and surprising improvement in the physical and chemical stability of the beneficial agent compound over other formulations.

BRIEF DESCRIPTION OF THE DRAWINGS

FIG. 1 is a cross-section of an implantable sustained release osmotic delivery device for use in combination with the concentrated suspensions of the present invention.

FIG. 2 is a graph illustrating the stability of a cytochrome c suspension.

FIG. 3 is a graph illustrating the stability of an $\alpha$-interferon suspension.

DESCRIPTION OF THE INVENTION

One aspect of this invention relates to preparations for stabilizing peptides and proteins at high concentrations for extended periods of time.

Another aspect of this invention relates to stabilized preparations of human $\alpha$-IFN.

Another aspect of this invention relates to stabilized preparations of human $\alpha$-IFN having concentrations of at least $1\times 10^9$ IU/ml.

Another aspect of this invention relates to stabilizing beneficial agent formulations comprising a beneficial agent having a particle size of between 0.3 to 50 microns and suspension vehicle formula having a viscosity between 100 to 100,000 poise at 37° C.

The new formulations are physically stable suspensions which provide chemical stability to water sensitive compounds and can be employed to stabilize high concentrations of the active compound. The carrier components are acceptable for use in implantable systems.

MODES FOR CARRYING OUT THE INVENTION

The concentrated beneficial agent suspensions of the present invention provide significantly stable concentrations over extended periods of time, useful for sustained delivery, implant applications. The suspensions of this invention minimize the particle degradation due to hydrolysis and particle settling over the duration of the extended delivery period. These extended periods of time are between one week to two years, preferably between three months to one year.

The sustained parenteral delivery of drugs provides many advantages. Typical sustained release implantable osmotic delivery devices are described in U.S. Pat. Nos. 5,034,229; 5,057,318; and 5,110,596 which are incorporated herein by reference. As shown in FIG. 1, these devices 10 typically comprise a housing 12 including a fluid impermeable wall section 14 and a fluid permeable wall section 16 which sections define and surround an internal compartment 18. An exit passageway 20 is formed within the fluid impermeable wall section to fluidly communicate the internal compartment 18 with the external environment. To minimize exposure to the environmental fluids, a beneficial agent 22 is contained within the fluid impermeable section. An expandable-driving member 24, contained within the fluid permeable section, expands with the imbibition of fluid across the fluid permeable wall section. Typically a piston 26 separates the beneficial agent 22 from the expandable driving member 24. This forces the agent out through the exit passageway and into the environment of use. The non-aqueous administration of a beneficial agent in the suspension formulation as disclosed herein can be accomplished using implant devices of these kinds.

According to this invention, high concentrations of the beneficial agent remain suspended, and physically and chemically stable in a non-aqueous suspension vehicle. "High concentration" is defined as the beneficial agent concentration level of at least about 0.5 wt % of the formulation, preferably at least about 5 wt % and most preferably between about 10 to 70% w/w. For example, "high concentrations" of α-IFN are $10^9$ to $10^{11}$; and for salmon calcitonin, concentrations of between $2 \times 10^4$ IU to $2.8 \times 10^6$ IU. The beneficial agent particle size is between 0.3 to 50 microns, and preferably about 1–10 microns in diameter. Desired particle size can be provided typically by milling, sieving, spray drying, supercritical fluid extraction of the particular beneficial agent selected. Typical beneficial agent for use in this device and composition include the interferons and calcitonin. Other representative beneficial agents that can be administered include pharmacologically active peptides and proteins, anabolic hormones, growth promoting hormones, hormones related to the endocrine system comprising porcine growth promoting hormone, bovine growth promoting hormone, equine growth promoting hormone, ovine growth promoting hormone, human growth promoting hormone, growth promoting hormones derived by extraction and concentration from pituitary and hypothalmus glands, growth promoting hormones produced by recombinant DNA methods, bovine growth promoting hormone as described in *Nucleic Acid Res.*, Vol. 10, p 7197 (1982), ovine growth promoting hormone as described in *Arch. Biochem. Biophys.*, Vol. 156, p 493 (1973), and porcine growth promoting hormone as described in DNA, Vol. 2, pp 37, 45, (1983). The polypeptides also comprise growth hormone, somatropin, somatotropin, somatotropin analogues, modified porcine somatotropin, modified bovine somatotropin, derivatives of both porcine and bovine somatotropin, somatomedin-C, gonadotropic releasing hormone, follicle stimulating hormone, luteinizing hormone, LH-RH, LH-RH analogs growth hormone releasing factor, gonadotropin releasing factor, insulin, colchicine, chorionic gonadotropin, oxytocin, somatotropin plus an amino acid, vasopressin, adrenocorticotrophic hormone, epidermal growth factor, prolactin, somatostatin, somatotropin plus a protein, cosyntropin, lypressin, polypeptides such as thyrotropin releasing hormone, thyroid stimulating hormone, secretin, pancreozymin, enkephalin, glucagon, endocrine agents secreted internally and distributed in an animal by way of the bloodstream, and the like. The beneficial agents and their dosage unit amounts are known to the prior art in *The Pharmacological Basis of Therapeutics*, by Gilman, Goodman, Rail and Murad, 7th Ed., (1985) published by MacMillan Publishing Co., NY; in *Pharmaceuical Sciences*, Remington, 17th Ed., (1985) published by Mack Publishing Co., Easton, Pa., and in U.S. Pat. No. 4,526,938.

Particularly preferred are beneficial agents which produce the desired therapeutic effect at a low delivery rate/dose, for example, proteins/peptides which require sub nanograms (programs) nanograms to milligrams of agent.

A pharmaceutically acceptable suspension vehicle is used to suspend the solid beneficial agent particles in the beneficial agent formulation. Non-aqueous vehicles are used to isolate the beneficial agent from water and prevent hydrolysis or other degradation of the beneficial agent while in suspension. Furthermore, pharmaceutically acceptable suspension vehicles may function as a thickening agent for the components present in an implant. As a vehicle for transporting beneficial agents from the implant, it provides protection against the decomposition of a beneficial agent, and it imparts physical and chemical stability to components present in the formulation. The thickening agent may be used to increase the viscosity of the formulation to prevent fluids in the implantation environment from mixing with the implant's beneficial agent formulation. The amount of thickening agent present in the formulation is between 1% to 99.9% and preferably 5–60% depending upon the viscosity adjustment needed.

Typical non-aqueous suspension vehicles include: waxes, which have a softening temperature at or less than body temperature; hydrogenated vegetable oils, (e.g., peanut oil, cottonseed oil, sesame oil, castor oil, olive oil, corn oil, lodinated poppy seed oils) silicon oil, medium chain fatty acid monoglycerides, or polyols. Of these polyols are preferred.

Polyols suitable for suspension vehicles include such as diol, triol, polyhydric alcohol, and the like. More specific polyols comprise polyethylene glycol (average molecular weight between 200 and 1000), propylene glycol, polyethylene glycol 1,5-pentylene glycol; 1,6-hexylene glycol; 1,7-heptylene glycol; 1,9-nonylene glycol; 1,2-dimethyl-1,6-hexylene glycol; 1,2,3-propanetriol; 1,2,5-pentanetriol; 1,3,5-pentanetriol; 1,2,4-butanetriol; dipentaerythriol, and the like. In another embodiment the pharmaceutically acceptable suspension vehicle comprises glycerol mono(lower alkyl) ethers and glycerol di(lower alkyl) ethers such as glycerol 1-methyl ether; glycerol 1-ethyl ether; glycerol 1,2-dimethyl ether; glycerol 1,3-dimethyl ether, and the like. In another embodiment the pharmaceutically acceptable vehicle comprises a mixture such as propylene glycol and glycerol; and the like.

Sufficient viscosity is required to suspend the particles in the carrier throughout the duration of the extended delivery period. Settling is a function of the particle size and the carrier viscosity. If the duration of the delivery period is shorter, the viscosity can be lower since the time required to be suspended is shorter. The viscosity required, for example, can be determined by the Stokes-Einstein equation which is a measure of how far a particle in suspension will travel $$V = \frac{2gR^2}{g\mu}(P_p - P_C)$$

V=velocity of settling
$\mu$=viscosity of the carrier
g=acceleration due to gravity
$P_p$=density of particle
$P_c$=density of carrier wherein R=the average particle radius of the beneficial agent. The viscosity of the beneficial agent suspending formulation can be altered by the use of thickening agents to raise the viscosity to the desired level. Typical thickening agents for use in the compositions of this invention include suitable hydrogels such as hydroxypropyl cellulose, hydroxypropyl methyl cellulose (HPMC), sodium carboxymethyl cellulose, polyacrylic acid, poly(methyl methacrylic acid) (PMMA). Preferred hydrogels are cellulose ethers such as hydroxyalkylcellulose and hydroxyalkylalkyl-cellulose compounds. A most preferred hydroxyalkylcellulose is hydroxypropyl cellulose (HPC) and povidone (PVP). Hydroxypropyl cellulose is commercially available in a wide range of viscosity grades sold under the tradename Klucel™ (Hercules, Ltd., London, England). The concentration of the hydroxyalkylcellulose is dependent upon the particular viscosity grade used and the desired viscosity of the liquid composition. For example, where the desired viscosity is less than about 1000 poise (cps), hydroxypropyl cellulose having an average molecular weight of about 60,000 daltons (i.e., Klucel EF™) can be used. Where the desired viscosity is from about 1000 to about 2500 cps, higher viscosity grades of hydroxypropyl cellulose can be used (i.e., Klucel LF™ and Lucel GF™). In addition to using different viscosities of different thickening agents, using different amounts of the same particular thickening agent can be used to vary the viscosity. Preferably, the concentration of hydroxypropyl cellulose is from 5 percent w/w and, more preferably from 5 to 20% w/w of the carrier and most preferably between 8–18% w/w. Aluminum monostearate can be used as a thickening agent if oils are used as the carrier.

Hydroxyalkylalkylcellulose ethers are a class of water-soluble hydrogels derived from etherification of cellulose. As used herein in reference to this class of hydrogels, the term "alkyl" means $C_1$–$C_6$ alkyl where alkyl refers to linear or branched chains having 1 to 6 carbon atoms, which can be optionally substituted as herein defined. Representative alkyl groups include methyl, ethyl, propyl, isopropyl, butyl, pentyl, hexyl and the like.

Exemplary hydroxyalkylalkylcelluloses are hydroxypropylmethyl cellulose, hydroxyethylmethyl cellulose and hydroxybutylmethyl cellulose. Hydroxypropylmethyl cellulose (HPMC) is preferred. HPMC is commercially available (i.e., Aldrich Chem. Co., Ltd. Dorset, England and Dow Chem. Co., Midland, Mich., USA) in a wide range of viscosity grades. In addition to increasing viscosity, hydroxyalkylalkylcelluloses can serve as a stabilizing, suspending and emulsifying agent. The concentration of hydroxyalkylalkylcellulose in a liquid composition of this invention is dependent inter alia on its intended use (i.e., stabilizer, emulsifier, viscosity-increasing agent) and its viscosity grade.

To assure the viscosity of the suspension vehicle is sufficient to maintain the agent in suspension over the desired delivery period, thickening agents can be added to the suspension vehicle. The preferred thickening agents include povidone and hydroxypropyl cellulose. In one embodiment, when the PEG utilized is a low molecular weight, e.g., 400, 5% hydroxypropyl cellulose, having an average molecular weight of 1000, or 40–60% povidone can be used in combination with a balance of polyethylene glycol. If the polyethylene glycol utilized in the suspension vehicle has a molecular weight of greater than 600, e.g. 1000 molecular weight, povidone is preferably utilized as the thickening agent.

The following examples are offered to illustrate the practice of the present invention and are not intended to limit the invention in any manner.

EXAMPLE 1

A viscous carrier was prepared containing 50% PEG 400 and 50% povidone (PVP) by weight. PEG 400 (Union Carbide) was weighed into a beaker and an equal weight of povidone K29-32 (GAF) was added. The PEG and povidone were mixed by stirring with a spatula for about 5 minutes. The blended carrier was allowed to sit overnight to insure complete dissolution of the povidone. The carrier was then deaerated in a vacuum oven (National Appliance Company) by drawing a vacuum and holding the carrier at 50° C. for 30 minutes.

Cytochrome c (Sigma, from horseheart) was milled in a jar mill and then passed through a 400 mesh screen to produce a particle diameter of less than 37 micron. In a beaker, 0.5566 grams of the cytochrome c was added to 4.9970 grams of the PEG 400/povidone carrier to prepare a 10% cytochrome c suspension in 50:50 PVP:peg 400 carrier. The suspension was thoroughly blended by mixing with a spatula for about 5 minutes. The cytochrome c suspension was then loaded into 11 osmotic veterinary implants (as in FIG. 1).

The implants were tested in vitro by releasing into culture tubes filled with deionized water. To monitor release of cytochrome c from the implants, samples of the release media were assayed on a UV spectrophotometer (Shimadzu UV 160U) at a wavelength of 409 nm. The implants delivered the cytochrome c successfully over the designed duration of the implant (42 days). FIG. 2 is a graph that illustrates the cumulative protein delivery (mg) overtime. During the later half of the release period, several implants were removed from to show that there was no settling of the cytochrome c had occurred. These implants were sectioned and samples of the protein suspension were removed from the top and bottom portions of the implant. The samples of the protein suspension were weighed, diluted with DI water in volumetric flasks and assayed via UV a spectrophotometer. Results indicated that the cytochrome c suspension was homogeneous.

EXAMPLE 2

Standard: 20 μl of a 8.0 mg/ml standard was diluted to 160 μg/ml. Each HPLC sample was diluted by a factor of 10 into distilled water. The operating conditions of the HPLC were as follows:

column: POROS RH 2.1 mm×3.0 cm

Mobile phase:A; 95% H2O, 0.1% TFA, 5% ACN B: 95% ACN,5% H2O, 0.083% TFA

Gradient: 20% B to 50% B in 5 minutes

Flow: 2.0 ml/min

Detector: 280 nm @ 0.002 AUFS

IRMA Standards Working standards were prepared by diluting IRMA standards into phosphate buffered saline (PBS) containing 0.5% Bovine Serum Albumin (BSA). Samples were prepared by serially diluting by factors of 400 for formulations and 2000 for the standard into PBS containing 0.5% BSA.

FIG. 3 shows the results of the HPLC and the IRMA assays. The HPLC measurements indicate no losses of the α-IFN over 5 says, even at 37° C. indicating stability of this protein non-aqueous vehicle. Relative to the initial stock solution, the activity shown by IRMA at t=0 is 78%. At t=5 days, the formulation displayed an activity of 87% at room temperature and 90% at 37° C. When compared to the original stock, no losses of α-IFN are detected by HPLC in this formulation. Stability of interferon in PEG over 5 days at 37° C. was indicated by this assay. However, approximately 80–90% of the activity of the initial stock was maintained, The IRMA readings suggest no activity losses due to time and temperature effects.

This invention has been described in detail with particular reference to certain preferred embodiments thereof, but it will be understood that variations and modifications can be effected within the spirit and scope of the invention.

What is claimed is:

1. A beneficial agent delivery device comprising a housing including a fluid impermeable wall section and a fluid permeable wall section, which sections define and surround an internal compartment, wherein the device delivers a formulation over an extended delivery period, and wherein the device contains a formulation comprising:

(a) at least 5% by weight beneficial agent in the form of solid particles having a particle size of 0.3 to 50 microns; and (b) a liquid suspension vehicle for suspending the particles in the formulation, wherein the liquid suspension formulation viscosity is sufficient to prevent settling of the agent in the liquid suspension formulation in the device over the extended delivery period.

2. A beneficial agent delivery device of claim 1, wherein the device is adapted to be implanted within an animal.

3. The device of claim 1 wherein the particle size is between 1 to 10 microns.

4. The device of claim 1 wherein the viscosity is 100 to 100,000 poise at 37° C.

5. The device of claim 1 wherein the extended delivery period is at least about 1 month.

6. The device of claim 1 wherein the beneficial agent is a water sensitive compound.

7. The device of claim 1 wherein the suspension vehicle comprises a low molecular weight polyol and a thickening agent.

8. The device of claim 7 wherein the polyol is polyethylene glycol having a molecular weight between 200 and 1000.

9. The device of claim 8 wherein the thickening agent comprises povidone.

10. The device of claim 7 wherein the polyol is polyethylene glycol having a molecular weight between 200 and 600.

11. The device of claim 10 wherein the thickening agent comprises povidone or hydroxypropyl cellulose.

12. The device of claim 1 wherein the beneficial agent is human α-interferon.

13. The device of claim 12 wherein the concentration of interferon is at least $1 \times 10^9$ IU.

14. A beneficial agent delivery device comprising a housing including a fluid impermeable wall section and a fluid permeable wall section, which sections define and surround an internal compartment, wherein the device delivers a formulation over an extended delivery period, and wherein the device contains a formulation comprising:

(a) 0.5 to 70% by weight beneficial agent in the form of solid particles having a particle size of 0.3 to 50 microns; and (b) a non-aqueous liquid vehicle comprising a non-aqueous vehicle for suspending the particles in the formulation, polyethylene glycol with a molecular weight of 200 to 1000, and a thickening agent, which is characterized by a formulation viscosity of 100 to 100,000 poise at 37° C. wherein said formulation viscosity is sufficient to prevent settling of the agent in the suspension formulation in the delivery device over the extended delivery period.

15. A beneficial agent delivery device of claim 14, wherein the device is adapted to be implanted within an animal.

16. The device of claim 14 wherein the particle size is between 1 to 10 microns.

17. The device of claim 14 wherein the extended delivery period is at least about 1 month.

18. A device according to claim 13 wherein the thickening agent is selected from the group consisting of povidone and hydroxypropyl cellulose.

19. The device of claim 14 wherein the beneficial agent is human α-interferon.

20. The device of claim 19 wherein the concentration of interferon is at least $1 \times 10^9$ IU.

21. The device of claim 14 wherein the beneficial agent is a water sensitive compound.

* * * * *